US012751730B2

(12) United States Patent
Tchulluian et al.

(10) Patent No.: US 12,751,730 B2
(45) Date of Patent: Oct. 6, 2026

(54) SYSTEMS AND METHODS FOR RESTORING BLOOD VESSEL PATENCY

(71) Applicant: Covidien LP, Mansfield, MA (US)

(72) Inventors: Onnik E. Tchulluian, Costa Mesa, CA (US); Ramesh V. Marrey, Mission Viejo, CA (US)

(73) Assignee: Covidien LP, Mansfield, MA (US)

( * ) Notice: Subject to any disclaimer, the term of this patent is extended or adjusted under 35 U.S.C. 154(b) by 682 days.

(21) Appl. No.: 18/145,364

(22) Filed: Dec. 22, 2022

(65) Prior Publication Data

US 2024/0206897 A1 Jun. 27, 2024

(51) Int. Cl.
*A61B 17/221* (2006.01)
*A61B 17/22* (2006.01)
(Continued)

(52) U.S. Cl.
CPC ............ *A61B 17/221* (2013.01); *A61F 2/958* (2013.01); *A61B 2017/22072* (2013.01); *A61M 25/104* (2013.01)

(58) Field of Classification Search
CPC ........ A61B 17/12131; A61B 17/12136; A61B 17/221; A61B 17/22031; A61B 2017/2212; A61B 2017/2215; A61B 2017/2217; A61B 2017/22034; A61B 2017/22035; A61M 25/00; A61M 25/0021; A61M 25/10; A61M 25/104; A61M 2025/09175; A61M 2025/09183; A61M 2025/1043; A61M 2025/1045; A61M 2025/1047; A61M 2025/105; A61M 2025/1052; A61M 2025/1054; A61M 2025/1056; A61M 2025/1059; A61M 2025/1061;
(Continued)

(56) References Cited

U.S. PATENT DOCUMENTS 6,142,987 A * 11/2000 Tsugita ................ A61M 25/09
604/509
2010/0087850 A1* 4/2010 Razack ............ A61B 17/32075
606/200
(Continued)

FOREIGN PATENT DOCUMENTS

WO 2022016096 A1 1/2022

*Primary Examiner* — Kankindi Rwego
(74) *Attorney, Agent, or Firm* — Fortem IP LLP

(57) ABSTRACT

A single treatment system for vascular defects can be configured for use in removing clot material via mechanical thrombectomy and/or for deployment of an expandable device at a lesion to treat intracranial atherosclerotic disease (ICAD). Such a treatment system can include a delivery catheter carrying an expandable member configured to be deployed for treatment of ICAD, such as a balloon or balloon-mounted stent. A thrombectomy assembly includes a mechanical thrombectomy device (e.g., a stent retriever) coupled to the distal end of a core member that is slidably disposed within the delivery catheter lumen. In operation, the thrombectomy device can be slidably advanced beyond a distal end of the delivery catheter lumen, where the thrombectomy device can expand and engage clot material. Additionally or alternatively, the expandable member carried by the delivery catheter can be deployed (e.g., expanded into apposition with the vessel wall) for treatment of ICAD.

19 Claims, 8 Drawing Sheets

(51) Int. Cl.
*A61F 2/958* (2013.01)
*A61M 25/10* (2013.01)

(58) Field of Classification Search
CPC .. A61M 2025/1063; A61M 2025/1065; A61M 2025/1068; A61F 2/95; A61F 2/958
USPC .......................................................... 606/159
See application file for complete search history.

(56) References Cited

U.S. PATENT DOCUMENTS

| | | | | |
|---|---|---|---|---|
| 2012/0116440 | A1 | 5/2012 | Leynov et al. | |
| 2014/0364896 | A1* | 12/2014 | Consigny ....... | A61B 17/320725 606/200 |
| 2015/0112376 | A1 | 4/2015 | Molaei et al. | |
| 2016/0354099 | A1 | 12/2016 | Turjman et al. | |
| 2017/0056061 | A1* | 3/2017 | Ogle .................... | A61B 17/221 |
| 2018/0085129 | A1* | 3/2018 | Hamuro .................... | A61F 2/01 |
| 2019/0029692 | A1 | 1/2019 | Ferrera et al. | |
| 2019/0167287 | A1 | 6/2019 | Vale et al. | |
| 2020/0390455 | A1 | 12/2020 | Nguyen et al. | |
| 2021/0321867 | A1 | 10/2021 | Cooper et al. | |
| 2021/0402157 | A1* | 12/2021 | Keating .......... | A61M 25/10181 |
| 2022/0015784 | A1 | 1/2022 | Erlick et al. | |
| 2022/0218372 | A1 | 7/2022 | Nguyen et al. | |

* cited by examiner

SYSTEMS AND METHODS FOR RESTORING BLOOD VESSEL PATENCY

TECHNICAL FIELD

The present technology relates generally to devices and methods for increasing or restoring patency to body lumens. Some embodiments of the present technology relate to devices and methods for removal of clot material from blood vessels and/or for treatment of atherosclerosis.

BACKGROUND

Blood vessels can become occluded by emboli, e.g., thrombi. For example, intracranial arteries can become occluded by thromboembolisms. Disruption of blood flow by the occlusion can prevent oxygen and nutrients from being delivered to tissues downstream of the occlusion. Deprivation of oxygen and nutrients to tissue distal to an occlusion can impair proper function of the tissue, and may result in cellular death. Cellular death increases with duration of the occlusion.

Blood flow can also be disrupted due to atherosclerosis, in which a build-up of plaque in the blood vessel reduces vessel patency and inhibits blood flow. In blood vessels in the brain, intracranial atherosclerotic disease (ICAD) can affect cerebral arteries and lead to strokes.

SUMMARY

Many physicians currently perform thrombectomies (i.e. clot removal) with stents to resolve ischemic stroke. Typically, the physician deploys a stent or other mechanical thrombectomy device into the clot in an attempt to push the clot to the side of the vessel and and/or retrieve the clot to re-establish blood flow. However, in some instances, what appears to be occlusion due to a thrombus may in fact be a stenotic region of a blood vessel due to intracranial atherosclerotic disease (ICAD). In such cases, blood flow may be improved upon initial deployment of the thrombectomy device, only for the blood flow to again be occluded once the thrombectomy device is retracted and the walls of the vessel resume their narrowed state. In such instances, the physician may determine that blood flow disruption is due to ICAD only when multiple passes of a thrombectomy device are unsuccessful. Following this determination, the physician may then choose to dilate the stenotic region using either balloon angioplasty or an implant such as a balloon-mounted stent. This involves retracting and removing the thrombectomy device from the treatment site, then delivering a guide wire past the stenotic region, and finally delivering either an angioplasty balloon or a balloon-mounted stent delivery system over the guide wire to the treatment site. As such, this approach requires the physician to re-navigate to the treatment site after removing the thrombectomy device.

Examples of the present technology provide a single treatment system capable of deploying both a mechanical thrombectomy device (e.g., a stent retriever) and/or an angioplasty device (e.g., an angioplasty balloon, balloon-mounted stent, or other suitable device). For instance, a delivery catheter carrying the angioplasty device can be positioned at or adjacent the treatment site. The mechanical thrombectomy device can be delivered through the delivery catheter to the treatment site. In operation, once the thrombectomy device is deployed and the clinician determines that balloon angioplasty and/or stenting is needed, the delivery catheter of the angioplasty balloon and/or stent can be distally advanced over the thrombectomy device to the treatment site. The angioplasty balloon or stent is then used to open the stenosis at the treatment site without retraction of the stent retriever. In this manner, the push wire of the thrombectomy device can serve as a guidewire over which the delivery catheter (carrying the angioplasty device) is advanced. This configuration allows for a single treatment system that can separately and/or sequentially deploy a thrombectomy device and/or an angioplasty device without requiring re-navigation to the treatment site.

Additionally or alternatively, this configuration allows for initial delivery and deployment of a mechanical thrombectomy device and then, in the event that thrombus removal is unsuccessful (e.g., due to ICAD), an angioplasty balloon and/or stent catheter can be advanced over the pushwire of the mechanical thrombectomy device to the treatment site, where the angioplasty balloon and/or stent can be deployed to open the stenosis without requiring the mechanical thrombectomy device to be removed. A further benefit of this approach is that the mechanical thrombectomy device, while in an expanded state in apposition with the vessel wall, can maintain positioning at the stenosis, thereby allowing for blood flow while the angioplasty balloon and/or stent catheter is being delivered.

The present technology is illustrated, for example, according to various aspects described below. Various examples of aspects of the present technology are described as numbered clauses for convenience. These are provided as examples and do not limit the present technology. It is noted that any of the dependent clauses may be combined in any combination, and placed into a respective independent clause. The other clauses can be presented in a similar manner.

Clause 1. A treatment system comprising: a delivery catheter assembly comprising: a tubular member defining a lumen and a distal opening and configured to be positioned intravascularly at or adjacent a treatment site; and an expandable member coupled to an outer surface of the tubular member, the expandable member configured to be expanded into apposition with a vessel wall at the treatment site increase patency of the vessel at the treatment site; and a thrombectomy assembly comprising: a core member disposed within the tubular member lumen, wherein the core member and tubular member are configured to slide relative to each other; and a thrombectomy device coupled to a distal end portion of the core member, wherein the thrombectomy assembly is configured to be slidably transitioned between a delivery configuration in which the distal end portion of the core member and the thrombectomy device are positioned within the lumen of the tubular member, and deployed configuration in which the distal end portion of the core member and the thrombectomy device are positioned outside of the lumen of the tubular member.

Clause 2. The system of clause 1, wherein in the delivery configuration, the thrombectomy device is in a compressed state in which an outer diameter of the thrombectomy device is equal to or less than an inner diameter of the lumen, and wherein in the deployed configuration the thrombectomy device is in an expanded state in which the outer diameter of the thrombectomy device is greater than an inner diameter of the lumen.

Clause 3. The system of clause 2, wherein the thrombectomy device is biased to self-expand from the compressed state to the expanded state.

Clause 4. The system of clause 3, wherein a proximal end of the thrombectomy device and the distal opening of the tubular member are configured to engage so that distally advancing distal opening of the tubular member relative to and toward the thrombectomy device with the thrombectomy device in the deployed configuration causes the thrombectomy device to transition from the deployed configuration to the delivery configuration.

Clause 5. The system of clause 4, wherein the thrombectomy device has a proximal taper to facilitate transitioning the thrombectomy device to the delivery configuration when proximally retracted to within the catheter lumen.

Clause 6. The system of any one of the preceding clauses, wherein the expanded member is configured to be expanded while the thrombectomy device is in the delivery configuration.

Clause 7. The system of clause 6, wherein the expanded member is configured to be expanded while the thrombectomy device is within the lumen and longitudinally overlapping at least of portion of the expanded member.

Clause 8. The system of clause 6 or clause 7, wherein the expanded member is configured to be expanded at or adjacent the treatment site while the thrombectomy device is within the lumen adjacent the treatment site.

Clause 9. The system of any one of the preceding clauses, wherein the expandable member comprises an angioplasty balloon.

Clause 10. The system of any one of the preceding clauses, wherein the expandable member comprises a balloon-mounted stent.

Clause 11. The system of any one of the preceding clauses, wherein the thrombectomy device comprises a stent retriever.

Clause 12. The system of any one of the preceding clauses, wherein proximal retraction of the core member relative to the tubular member moves the interventional element from the expanded state while distal to the tubular member lumen to the low-profile state while disposed within the tubular member lumen.

Clause 13. A method comprising: disposing an interventional element coupled to a distal end portion of a core member within a blood vessel such that the interventional element is at or adjacent a thrombus, wherein the core member extends through a lumen of a tubular member and the interventional element is disposed distal to a distal opening of the tubular member; moving the tubular member and/or the core member to position the interventional element within the tubular member lumen; after positioning the interventional element within the tubular member lumen, expanding an expandable member carried by the tubular member into apposition with the vessel wall at the treatment site.

Clause 14. The method of clause 13, wherein moving the tubular member and/or the core member comprises proximally retracting the core member relative to the tubular member.

Clause 15. The method of clause 13 or clause 14, wherein moving the tubular member and/or the core member comprises distally advancing the tubular member relative to the core member.

Clause 16. The method of any one of clauses 13-15, wherein the interventional element assumes an expanded state when disposed distal to the distal opening of the tubular member, and wherein the interventional element assumes a low-profile state when positioned within the tubular member lumen.

Clause 17. The method of any one of clauses 13-16, wherein expanding the expandable member comprises inflating an angioplasty balloon.

Clause 18. The method of any one of clauses 13-17, wherein expanding the expandable member comprises inflating a balloon to deploy a balloon-mounted stent at the treatment site.

Clause 19. A method comprising: expanding a mechanical thrombectomy device at a treatment site within a blood vessel; after expanding the mechanical thrombectomy device, moving the mechanical thrombectomy device to a collapsed configuration within a catheter lumen disposed within the blood vessel; after retracting the mechanical thrombectomy device to within the catheter lumen, expanding an expandable device carried by the catheter into apposition with the vessel wall at the treatment site.

Clause 20. The method of clause 19, further comprising, after expanding the expandable device, removing the catheter and the mechanical thrombectomy device from the blood vessel.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

DETAILED DESCRIPTION

I. Select Embodiments of Treatment Systems and Devices

As noted above, it can be advantageous to provide a single treatment system capable of deploying both a mechanical thrombectomy device (e.g., a stent retriever) and an angioplasty device (e.g., an angioplasty balloon, balloon-mounted stent, or other suitable device) to an intravascular treatment site. This can be particularly beneficial in instances in which a treatment site may be either a lesion (e.g., a stenotic region of a blood vessel) or an occluded portion of a vessel due to a thrombus, as these two cases may be difficult to distinguish under conventional visualization and diagnostic techniques. Providing a single treatment system that can deploy a mechanical thrombectomy device and then, if mechanical thrombectomy is unsuccessful, deploy an angioplasty device, can reduce the complexity of interventional procedures and improve the success rate in restoring patency to the affected blood vessel.

Figure 1A:
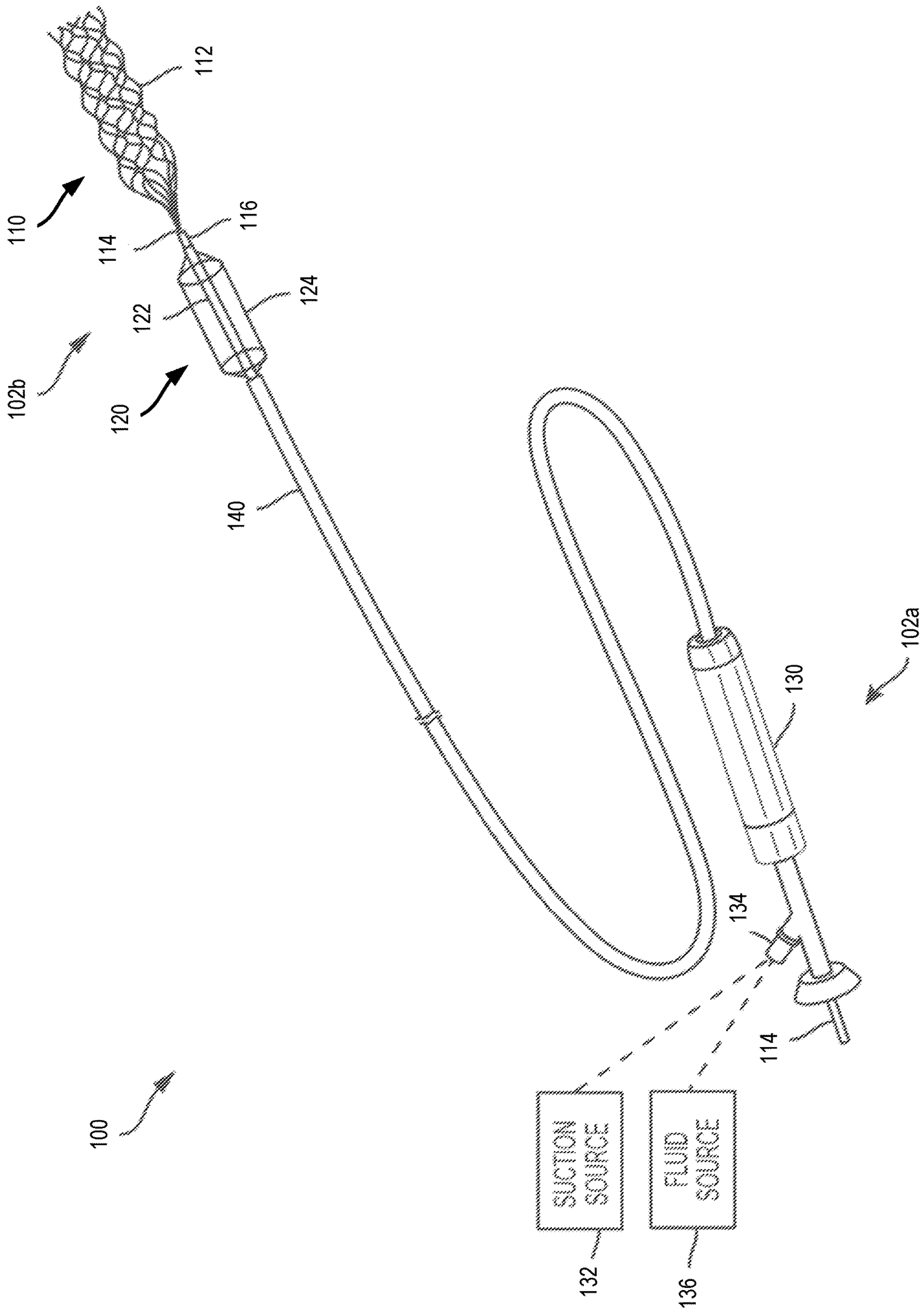
FIG. 1A shows a perspective view of a treatment system for restoring patency to a blood vessel, in accordance with one or more embodiments of the present technology.

FIG. 1A illustrates a treatment system 100 for restoring patency to a bodily lumen according to one or more embodiments of the present technology. As shown in FIG. 1A, the system 100 can include a proximal portion 102*a* and a distal portion 102*b* configured to be intravascularly positioned within a blood vessel (such as an intracranial blood vessel) at a treatment site (e.g., at or adjacent a thrombus, a lesion such as a stenotic region of a blood vessel, or other suitable treatment site). The treatment system 100 can include a thrombectomy assembly 110 that can be slidably disposed within a delivery catheter assembly 120. A proximal handle 130 is disposed at the proximal portion 102*a* of the treatment system 100, and can be operably coupled to the thrombectomy assembly 110 and/or the delivery catheter assembly 120. As shown in FIG. 1A, the system 100 may additionally include a suction source 132 (e.g., a syringe, a pump, etc.) configured to be fluidly coupled (e.g., via a connector 134) to one or more components of the treatment system 100 (e.g., a catheter) to apply negative pressure therethrough. In some embodiments, the system 100 also includes a fluid source 136 (e.g., a fluid reservoir, a syringe, pump, etc.) configured to be fluidly coupled (e.g., via the connector 134) to one or more components of the treatment system 100 (e.g., a catheter) to supply fluid (e.g., saline, contrast agents, a drug such as a thrombolytic agent, etc.) thereto.

The thrombectomy assembly 110 includes a thrombectomy device 112 (e.g., an expandable device such as a stent retriever) coupled to distal end portion of a core member 114. The core member 114 may include an elongate body, for example a wire, tube (e.g., a hypotube), combinations thereof, or other suitable structure for pushing, pulling, and/or otherwise manipulating the thrombectomy device 112. In operation, the thrombectomy device 112 can be deployed at or adjacent a thrombus in a blood vessel, and the thrombectomy device 112 can be configured to engage, interlock with, grasp, or otherwise facilitate capture and removal of the thrombus. The thrombectomy device 112 can then be proximally retracted to remove the thrombus from the blood vessel and restore blood flow therethrough.

The core member 114 can extend between the thrombectomy device 112 and the proximal portion 102*a* of the treatment system 100. Optionally, the thrombectomy assembly 110 further includes a microcatheter 116 which slidably receives the core member 114 therein. The microcatheter 116 can be configured to be positioned over the thrombectomy device 112 while the thrombectomy device 112 is in a low-profile, constrained configuration. To deploy the thrombectomy device 112, the microcatheter 116 can be proximally retracted relative to the thrombectomy device 112 (and/or the thrombectomy device 112 can be distally advanced relative to the microcatheter 116). Once the thrombectomy device 112 is positioned outside the microcatheter 116, the thrombectomy device may self-expand into the expanded, unconstrained configuration as shown in FIG. 1A. In some embodiments, the microcatheter 116 can be omitted, and the thrombectomy device 112 can instead be constrained and received within the delivery catheter or another tubular member.

The delivery catheter assembly 120 includes a delivery catheter 122 and an expandable member 124 carried by a distal portion of the delivery catheter 122. The expandable member 124 can be an angioplasty device configured to treat atherosclerosis. Examples of such devices include angioplasty balloons, balloon-mounted stents, self-expandable stents, or any other suitable angioplasty device. The delivery catheter 122 can include an inflation lumen (not shown in FIG. 1A) that enables the expandable member 124 to be inflated or collapsed via injection of fluid and/or removal of fluid by a clinician. As described in more detail below, the expandable member 124 can be selectively expanded at a treatment site (e.g., a stenotic region of a blood vessel) to dilate an affected blood vessel and restore patency. In operation, the core member 114 of the thrombectomy assembly 110 can be slidably disposed within the lumen of the delivery catheter 122. By proximally retracting the core member 114 relative to the delivery catheter 122 (or distally advancing the delivery catheter 122 relative to the core member 114), the thrombectomy device 112 can be disposed within the lumen of the delivery catheter 122 while in its low-profile, constrained configuration.

As noted above, the treatment system 100 can include the microcatheter 116 and the delivery catheter 122. In some examples, the system 100 can additionally include a guide catheter 140, which can be sized and configured to slidably receive the delivery catheter 122 within its lumen. As such, the delivery catheter 122 can be slidably disposed within the lumen of the guide catheter 140, the microcatheter 116 can be slidably disposed within the lumen of the delivery catheter 122, and the core member 114 can be slidably disposed within the lumen of the microcatheter 116.

With continued reference to FIG. 1A, some or all of the catheters (e.g., microcatheter 116, delivery catheter 122, and/or guide catheter 140) can each be formed as a generally tubular member extending along and about a central axis and terminating at a respective distal end. The guide catheter 140 may be a balloon-guide catheter having an inflatable balloon or other expandable member (e.g., at or near the distal end thereof) that can be used to anchor the guide catheter 140 with respect to a surrounding vessel. In some embodiments, the guide catheter 140 does not include an expandable member. The delivery catheter 122 and/or the microcatheter 116 may be generally constructed to track over a conventional guidewire in the cervical anatomy and into the cerebral vessels associated with the brain. The delivery catheter 122 and/or the microcatheter 116, for example, can each have a length that is at least 125 cm long, and more particularly may be between about 125 cm and about 175 cm long. Other designs and dimensions are contemplated.

According to some embodiments, the bodies of the catheters can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheters or an adjacent surface with a hydrophilic material such as polyvinylpyrrolidone (PVP) or some other plastic coating. Additionally, either surface can be coated with various combinations of different materials, depending upon the desired results.

Figure 1B:
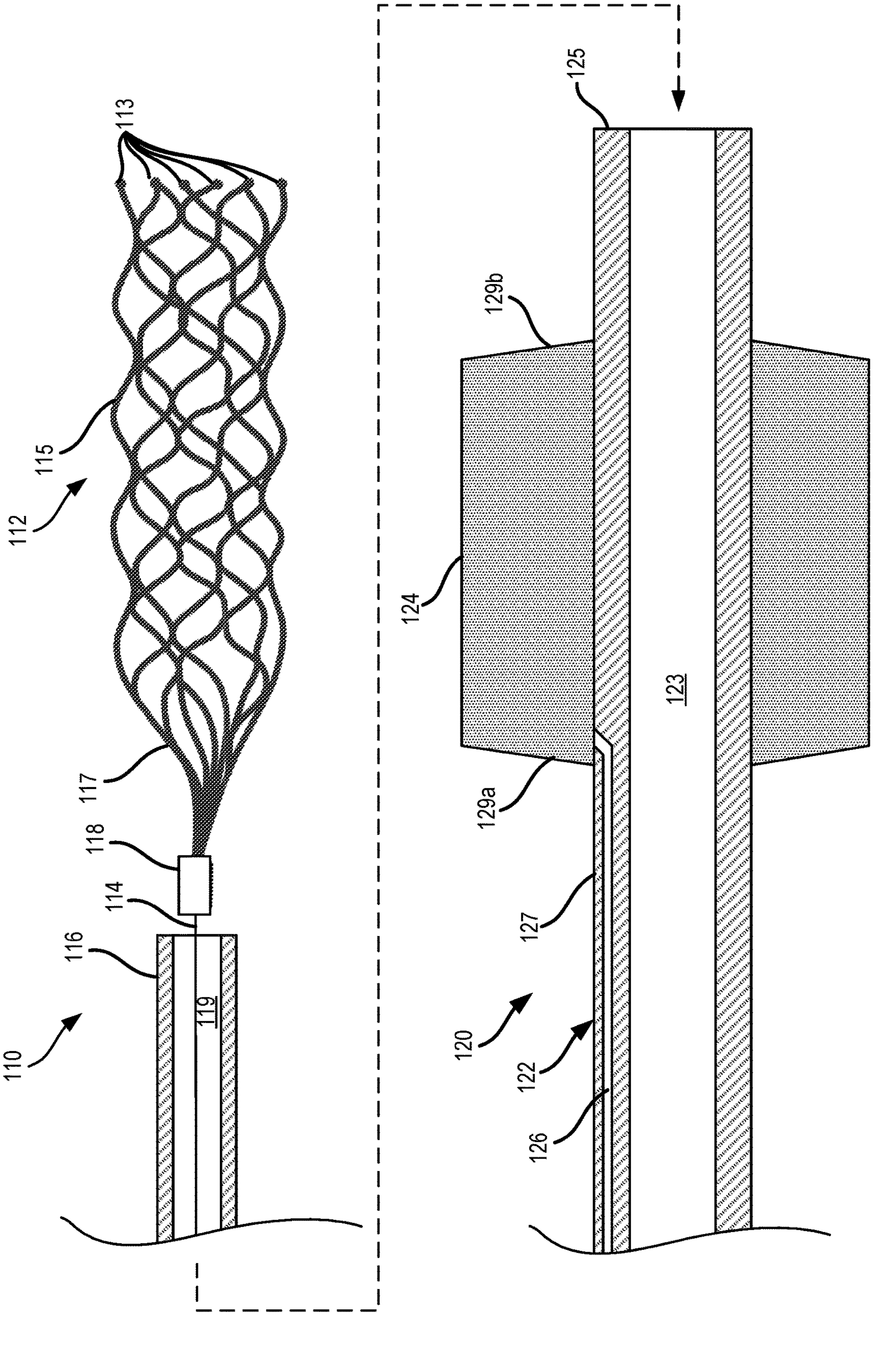
FIG. 1B shows an enlarged detail view of a portion of the treatment system shown in FIG. 1A.

FIG. 1B illustrates a side, cross-sectional, enlarged detail view of a portion of the treatment system 100 shown in FIG. 1A, with the thrombectomy assembly 110 and the delivery catheter assembly 120 shown separately for clarity. In operation, at least a portion of the thrombectomy assembly 110 can be slidably received within a lumen 123 of the delivery catheter 122, as reflected by the dashed line in FIG. 1B.

As noted above, the thrombectomy assembly 110 includes a thrombectomy device 112 coupled to a distal end portion of a core member 114 (e.g., a pushwire, hypotube, or other suitable elongate manipulation member). In some embodiments, the core member 114 is coupled to the thrombectomy device 112 at a connection point 118. In various embodiments, the connection point 118 can take any suitable form, such as a snap-fit engagement, a crimped tubular member, a laser weld, etc. Optionally, the connection point 118 can be radiopaque to facilitate visualization under fluoroscopy. As shown in FIG. 1B, the thrombectomy assembly 110 can also include a microcatheter 116 having a lumen 119 configured to slidably receive the core member 114 and/or the thrombectomy device 112 therein. In various examples, the microcatheter 116 can be omitted, and the core member 114 and the thrombectomy device 112 may instead be slidably received directly within the lumen of the delivery catheter 122.

The thrombectomy device 112 can be, for example, an expandable member, a self-expandable stent, basket, mesh, filter, or other suitable structure. In various embodiments, the thrombectomy device 112 can have a low-profile state for delivery through the microcatheter 116 and an expanded state when it is released from the microcatheter 116 or otherwise deployed at the treatment site. In the expanded state, the thrombectomy device 112 can have a radially outermost dimension that is greater than that of the core member 114. For example, the thrombectomy device 112 can have a radially outermost dimension sized and configured to permit the thrombectomy device 112 to come into contact with the vessel wall at the treatment site.

In various examples, the thrombectomy device 112 can include one or more radiopaque markers 113 to facilitate visualization under fluoroscopy. In some implementations, providing a plurality of radiopaque markers 113 allows a clinician to determine visually the thrombectomy device 112 is expanded radially when deployed within a blood vessel. For example, by arranging radiopaque markers 113 along various struts, wires, or other structures within the thrombectomy device 112, the individual radiopaque markers 113 may be radially closer together when the thrombectomy device 112 is in its low-profile, constrained state, and the individual radiopaque markers 113 may be radially separated from one another when the thrombectomy device 112 assumes the expanded state. In some examples, the radiopaque markers 113 can be disposed at a distal end portion of the thrombectomy device 112. The radiopaque markers 113 can include marker bands, coils, or other structures made of radiopaque material such as platinum, platinum-iridium, gold, or other suitable material.

The thrombectomy device 112 can have a low-profile, constrained or compressed configuration (not shown in FIG. 1B) for intravascular delivery to the treatment site within the microcatheter 116, and an expanded configuration for securing and/or engaging clot material and/or for restoring blood flow at the treatment site. The thrombectomy device 112 may self-expand from the low-profile configuration to the expanded configuration upon translation from inside of to outside of the microcatheter 116. In some embodiments, the thrombectomy device 112 comprises a laser-cut stent, a braid formed of a plurality of wires (e.g., filaments, threads, sutures, fibers or the like) that have been interwoven to form a structure having openings, or any other suitable structure. The thrombectomy device 112 can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate, polyactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium. In certain embodiments, metal filaments may be highly polished and/or surface treated to further improve their hemocompatibility.

In some embodiments, the thrombectomy device 112 may comprise an open cell framework or body and a coupling region extending proximally from the body. In some embodiments, a distal portion 115 of the thrombectomy device 112 can be generally tubular (e.g., cylindrical), and the 117 proximal portion of the thrombectomy device 112 tapers proximally to the connection point 118. The proximal taper to the coupling region can permit a small-diameter coupling region to serve as an attachment point for the thrombectomy device 112 even though a distal portion of the thrombectomy device 112 has a significantly larger diameter than the coupling region. Additionally or alternatively, the proximal taper can facilitate resheathing of the thrombectomy device 112, such as by proximally retracting the thrombectomy device 112 into a surrounding catheter. In some embodiments, the thrombectomy device 112 is a mesh structure formed of a superelastic material (e.g., Nitinol) or other resilient or self-expanding material configured to self-expand when released from the microcatheter 116. For example, in some embodiments the thrombectomy device 112 may be a stent and/or stentriever, such as Medtronic's Solitaire™ Revascularization Device, Stryker Neurovascular's Trevo® ProVue™ Stentriever, or other suitable devices. In other embodiments, the thrombectomy device 112 may include a plurality of braided filaments. Examples of a suitable expandable member 210 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

In some embodiments, some or all of the thrombectomy device 112 is formed by drawn-filled tube ("DFT") wires having a radiopaque core (e.g., platinum, tantalum, gold, tungsten, etc.) surrounded by a superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires.

With continued reference to FIG. 1B, the delivery catheter assembly 120 includes the delivery catheter 122 which carries the expandable member 124. As noted previously, the expandable member 124 can be an angioplasty device configured to treat narrowing of the blood vessel, for example due to atherosclerosis. Examples of such devices include angioplasty balloons, balloon-mounted stents, self-expandable stents, drug-eluting balloon-mounted or self-expanding stents, or any other suitable angioplasty device. The delivery catheter 122 can include an inflation lumen 126 that enables the expandable member 124 to be inflated or collapsed via injection of fluid (e.g., saline, a gas, etc.) and/or removal of fluid by a clinician. In various examples, the inflation lumen 126 can extend along a length of the delivery catheter 122 and be fluidically coupled at a proximal end portion of the delivery catheter 122 to fluid source 136 (FIG. 1A) and/or to suction source 132 (FIG. 1A). Although the inflation lumen 126 is shown extending along the wall of the delivery catheter 122, in various embodiments the inflation lumen 126 can assume other configurations, for example being formed in a separate inflation tube that extends alongside the delivery catheter 122.

The delivery catheter 122 also defines a delivery lumen 123 which is sized and configured to receive the thrombectomy assembly 110 therein. For instance, the delivery lumen 123 can have a lumen diameter that is greater than an outer diameter of the microcatheter 116. The thrombectomy device 112 can be configured to be received within the delivery lumen 123, for example while in an at least partially constrained, low-profile configuration. In the illustrated example, the proximal taper at the proximal portion 117 of the thrombectomy device 112 can facilitate the collapse and resheathing of the thrombectomy device 112 within the delivery catheter lumen 123. For instance, the delivery catheter 122 can be introduced into the anatomy over the proximal end of the core member 114 of the thrombectomy device 112, and the delivery catheter 122 can then be distally advanced to the treatment site. As the delivery catheter 122 is distally advanced relative to the thrombectomy device 112 (and/or the thrombectomy device 112 is proximally retracted relative to the delivery catheter 122), a distal end 125 of the delivery catheter 122 contacts the proximal portion 117 of the thrombectomy device 112. As the distal end 125 of the delivery catheter 122 continues to be advanced distally, the thrombectomy device 112 is moved into the lumen 123 of the delivery catheter 122 and assumes a low-profile, constrained configuration.

The expandable member 124 can take the form of a compliant, resilient member mounted to an exterior surface 127 of the delivery catheter 122, for example extending circumferentially around the exterior surface 127 of the delivery catheter 122. In the illustrated example, the expandable member 124 is a generally cylindrical body with tapering proximal and distal portions 129*a* and 129*b*. However, the particular shape and configuration of the expandable member 124 can vary, and may assume any suitable form. The length, outermost diameter in the expanded state, and/or shape of the expandable member 124 can be selected depending on the anatomy of the treatment site (e.g. vessel diameter, length of lesion, etc.). In some instances, the expandable member 124 can be a balloon that includes one or more cutting or scoring elements (e.g., blades, wires, etc.) disposed on the balloon surface to enhance displacement of plaque at the treatment site. Additionally or alternatively, the expandable member 124 can include or have disposed thereon one or more liners, coatings, therapeutic agents (e.g., antithrombogenic coatings or drugs, antirestenotic coatings or drugs), etc.

In use, the expandable member 124 can be selectively expanded at a treatment site (e.g., a stenotic region of a blood vessel) to restore patency. The radially outward force of the expandable member 124 can be sufficient to dislodge and/or compress plaque or other buildup at the vessel site, such that after removal of the expandable member 124, the blood vessel lumen is wider than before the intervention. In some examples, the expandable member 124 can be or include a permanent implant, such as a tubular stent. For instance, a tubular stent can be mounted over a balloon and retained in a compressed configuration until the balloon is expanded (e.g., via inflation via delivery of saline through inflation lumen 126), at which point the balloon expansion forces the stent into an expanded state and into apposition with the vessel wall. The stent (or other suitable implant) can remain in the expanded state and in apposition with the vessel wall even after the balloon is collapsed (e.g., by withdrawing saline from the balloon via the inflation lumen 126). In various examples, the stent can be a tubular mesh formed of a laser-cut tube or sheet, braided wires or filaments, combinations thereof, or any other suitable technique. The length, outermost diameter in the expanded state, radially outward force, and/or shape of such a tubular stent can be selected depending on the anatomy of the treatment site (e.g. vessel diameter, length of lesion, etc.).

In operation, the thrombectomy assembly 110 may first be advanced intravascularly to the treatment site, for instance with the thrombectomy device 112 radially constrained within a surrounding microcatheter. The thrombectomy device 112 can then be deployed (e.g., by proximally retracting the microcatheter) such that it expands into apposition with the vessel wall. This expansion may result in improvement or restoration of blood flow through the treatment site. However, if retraction of the thrombectomy device 112 causes blood flow to again become impeded and/or no thrombus material is removed with retraction of the thrombectomy device 112, this can indicate that the stenosis is due to ICAD rather than a thrombus. In such a scenario, the clinician may leave the thrombectomy device 112 in position at or near the treatment site (optionally re-positioning the thrombectomy device 112 so that it is in an expanded configuration at the stenosis, thereby permitting blood flow therethrough). The delivery catheter assembly 120 can then be slidably advanced in a distal direction over the core member 114 of the thrombectomy assembly 110 until the expandable member 124 carried by the delivery catheter 122 is positioned at or adjacent the treatment site. In this approach, the core member 114 of the thrombectomy assembly 110 effectively serves as a guidewire for distal advancement of the delivery catheter assembly 120 to the treatment site. As a result of this distal advancement of the delivery catheter 122 over the thrombectomy device 112, the thrombectomy device 112 can be urged into a low-profile, radially constrained state within the lumen of the delivery catheter 122. The expandable member 124 can then be deployed (i.e., radially expanded into apposition with the vessel wall at the stenotic region), thereby increasing patency of the blood vessel. Finally, the delivery catheter assembly 120 and the thrombectomy assembly 110 can each be removed by proximally retracting these assemblies and withdrawing them from the body.

In some implementations, the thrombectomy assembly 110 can initially be slidably disposed within the lumen 123 of the delivery catheter 122 of the delivery catheter assembly 120. The system 100 can then be advanced to an intravascular treatment site (e.g., a thrombus, a lesion, etc.). The treatment system 100 enables a clinician to perform one or both of a mechanical thrombectomy procedure (by deploying the thrombectomy device 112) and an angioplasty procedure (by deploying the expandable member 124). This can be particularly beneficial in instances in which a clinician is unable to definitively determine whether reduced blood flow observed in a patient is due to a thrombus or atherosclerosis. Example methods of using the treatment system 100 are described in more detail below.

II. Select Methods of Use

Figures 2A, 2B, 2C:
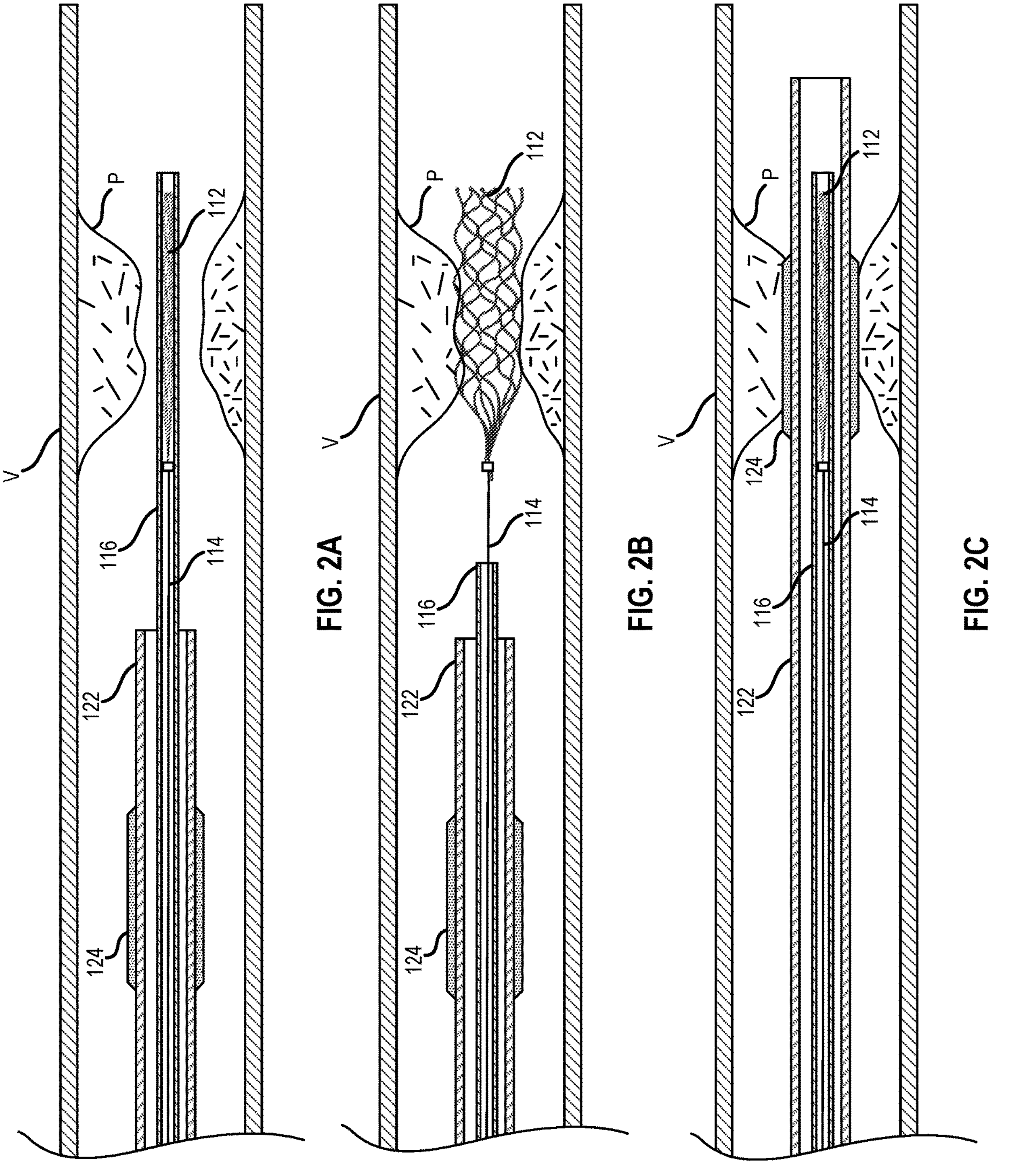
FIGS. 2A-2E show side cross-sectional views of using a treatment system to restore patency to a blood vessel in accordance with embodiments of the present technology.

FIGS. 2A-2E illustrate a method of restoring patency to a blood vessel V using the treatment system 100 of the present technology. As shown in FIG. 2A, the system 100 can be positioned within the vessel V such that a distal end portion of the microcatheter 116 is disposed at the treatment site, which in this case is a build-up of plaque P that has caused a narrowing of the lumen of the blood vessel V. The thrombectomy device 112 is disposed within the microcatheter 116 and held in a constrained state. The core member 114, which is coupled to the thrombectomy device 112, extends proximally along the lumen of the microcatheter to permit a clinician to manipulate the thrombectomy device 112 (e.g., pushing and pulling the thrombectomy device 112 relative to the microcatheter 116).

As noted previously, in some instances a clinician may observe occluded blood flow downstream of the treatment site, and yet be unable to determine whether the treatment site is a lesion (e.g., a stenotic region of a blood vessel) or an occluded portion of a vessel due to a thrombus, as these two cases may be difficult to distinguish under conventional visualization and diagnostic techniques. Using the treatment system 100 of the present technology, a clinician may first attempt a thrombectomy procedure to remove a blood clot (if present). If the thrombectomy procedure is unsuccessful (e.g., blood flow is not improved or restored after one or more passes of the thrombectomy device 112 through the treatment site), the clinician may proceed with an angioplasty procedure using the expandable member 124. If, however, the thrombectomy procedure is successful (e.g., blood flow is improved after one or more passes of the thrombectomy device 112, indicating that a blood clot has been successfully removed from the treatment site), then the clinician may retract the treatment system 100 from the treatment site without deploying the expandable member 124.

As seen in FIG. 2A, the delivery catheter 122 can be disposed adjacent but spaced apart from the treatment site, for example being disposed proximal to the plaque P. The microcatheter 116 is slidably disposed within the lumen of the delivery catheter 122, and can be advanced distally beyond a distal end of the delivery catheter 122, such that the thrombectomy device 112 is at a position longitudinally aligned with the treatment site.

In FIG. 2B, the microcatheter 116 has been proximally retracted, permitting the thrombectomy device 112 to self-expand into the expanded configuration. In this state, the thrombectomy device 112 can expand into apposition with the plaque P and/or with the walls of the vessel V. As noted previously, in some instances this expansion of the thrombectomy device 112 can temporarily restore or otherwise improve blood flow through the vessel V, even if the improvement ceases once the thrombectomy device 112 is removed (e.g., proximally retracted from the treatment site). In at least some cases, this is because the thrombectomy device 112 temporarily displaces the plaque P and increases blood vessel patency, but the radially outward force of the thrombectomy device 112 may be insufficient to permanently compress or displace the plaque P to dilate the blood vessel. Accordingly, use of an angioplasty device such as expandable member 124 may be indicated in such circumstances.

Accordingly, as shown in FIG. 2C, the clinician can deploy an angioplasty device by advancing the delivery catheter 122 over the thrombectomy device 112. This can optionally include first distally advancing the microcatheter 116 over the thrombectomy device 112, and then advancing the delivery catheter 122 over the microcatheter 116. Alternatively, the microcatheter 116 and the delivery catheter 122 can be advanced together over the thrombectomy device 112. In still other embodiments, the microcatheter 116 need not be advanced over the thrombectomy device 112, and instead the delivery catheter 122 can be advanced over the thrombectomy device 112. In each instance, the thrombectomy device 112 can be received into a catheter lumen, and may assume a low-profile, constrained configuration to be fully disposed within the surrounding lumen. In various examples, the proximal taper of the thrombectomy device 112 can facilitate this resheathing of the thrombectomy device 112 within a surrounding catheter.

In the arrangement shown in FIG. 2C, the expandable member 124 is positioned adjacent (e.g., axially aligned with) the treatment site. In some instances, this placement can be more easily achieved because the thrombectomy device 112 serves as an anchor and guide for final placement of the expandable member 124.

Figure 2D:
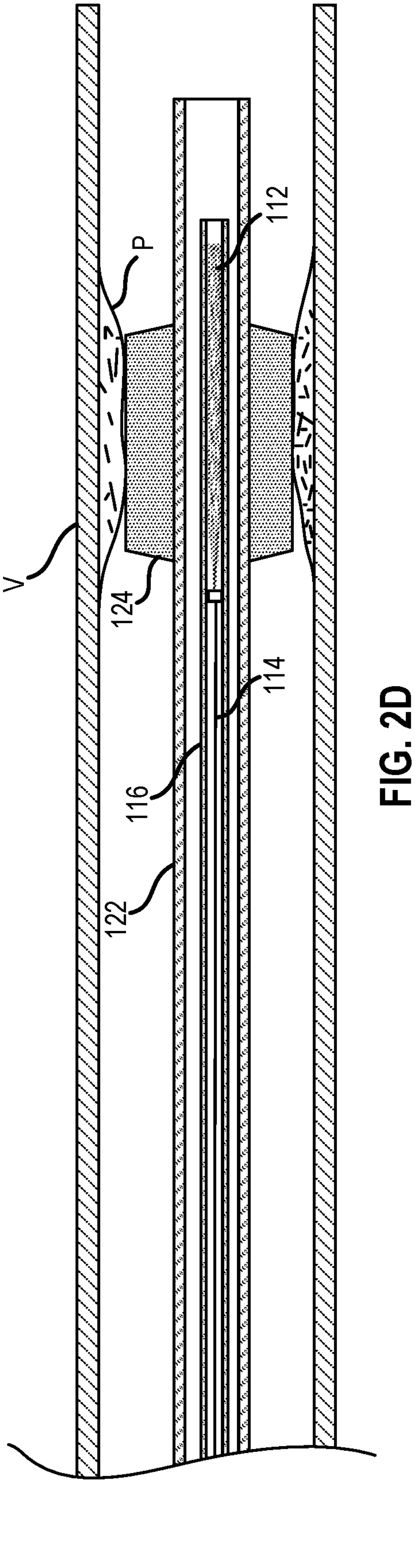
Figure 2E:
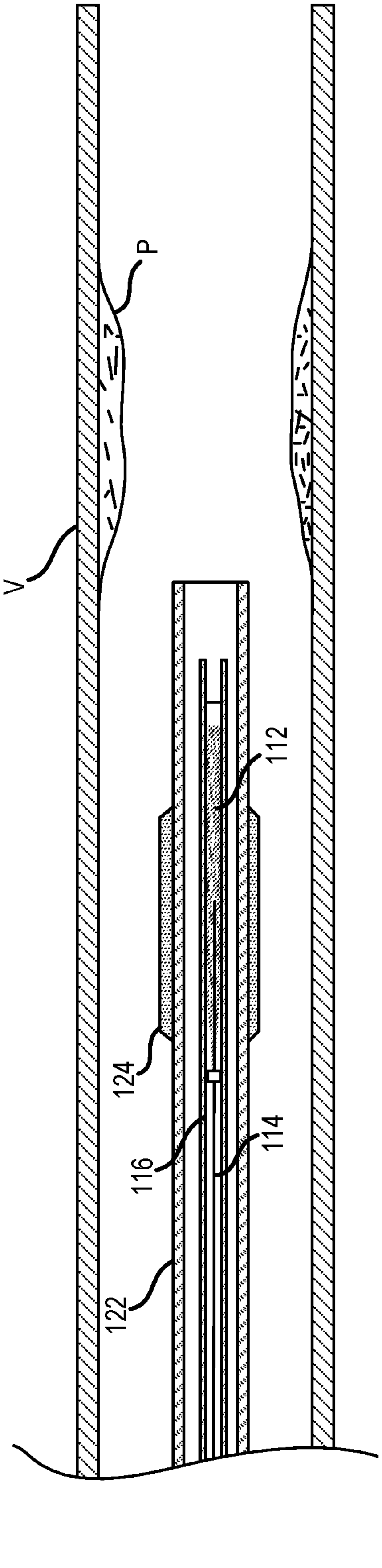

In FIG. 2D, the expandable member 124 is expanded (e.g., via an inflation lumen). This expansion can cause the plaque P to be compressed and/or displaced, thereby increasing patency of the blood vessel V. Next, as shown in FIG. 2E, the expandable member 124 can be returned to its unexpanded form (e.g., by removing fluid therefrom via the inflation lumen), and the delivery assembly and thrombectomy assembly can together be removed by proximally retracting them through the blood vessel V.

While the configuration shown in FIGS. 2A-2B depicts the delivery catheter 122 positioned within the vessel V at a position proximal to the plaque P while the thrombectomy device 112 is positioned radially adjacent the plaque P, in various embodiments the delivery catheter 122 may not be introduced into the vessel V and/or advanced to a position near the treatment site until after the thrombectomy device 112 has been deployed and a clinician has determined that the thrombectomy device 112 is inadequate to restore patency to the blood vessel (e.g., the occlusion is due to plaque or ICAD rather than a thrombus). In such scenarios, the thrombectomy device 112 may first be deployed at the site of the plaque P, such as by proximally retracting the microcatheter 116 similar to the state shown in FIG. 2B. Then, while the thrombectomy device 112 remains in the deployed state at the site of the plaque P, the delivery catheter 122 can be introduced into the vessel V, for instance by being positioned over a proximal end of the core member 114 and slidably advanced in the distal direction until the expandable member 124 is positioned at or near the treatment site (similar to the configuration shown in FIG. 2C). With this technique, the delivery catheter 122 is only introduced into the vessel V if the thrombectomy device 112 is unable to effectively retore blood flow at the treatment site.

Figure 3A:
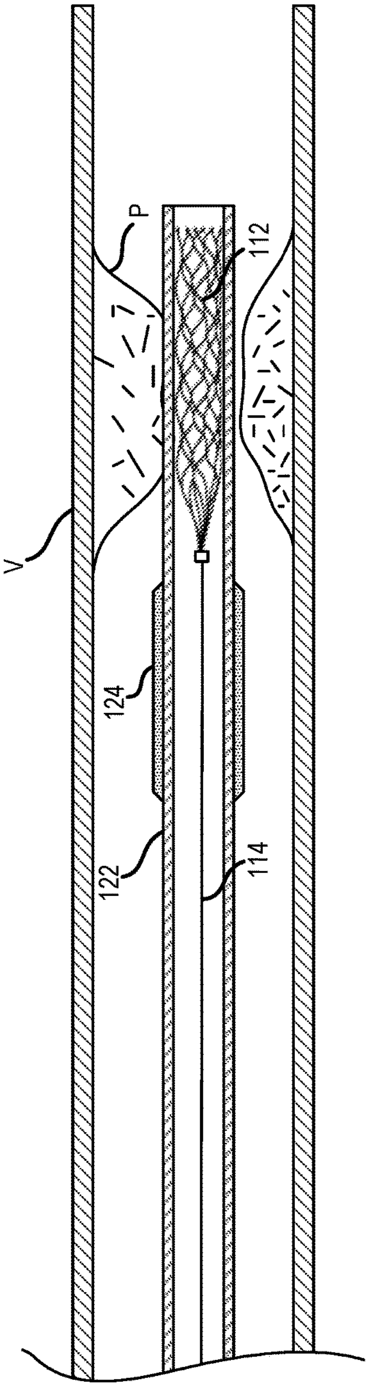
FIGS. 3A-3E show side cross-sectional views of using a treatment system to restore patency to a blood vessel in accordance with embodiments of the present technology.

FIGS. 3A-3E illustrate another method of restoring patency to a blood vessel V using the treatment system 100 of the present technology. In the method shown in FIGS. 3A-3E, the process can be similar to that shown in FIGS. 2A-2E, except that the microcatheter 116 is omitted. As shown in FIG. 3A, the system 100 can be positioned within the vessel V such that a distal end portion of delivery catheter 122 is disposed at the treatment site (denoted by the build-up of plaque P that has caused a narrowing of the lumen of the blood vessel V). The thrombectomy device 112 is disposed within the delivery catheter 122 and held in a constrained state. The core member 114, which is coupled to the thrombectomy device 112, extends proximally along the lumen of the delivery catheter 122 to permit a clinician to manipulate the thrombectomy device 112 (e.g., pushing and pulling the thrombectomy device 112 relative to the delivery catheter 122).

Figure 3B:
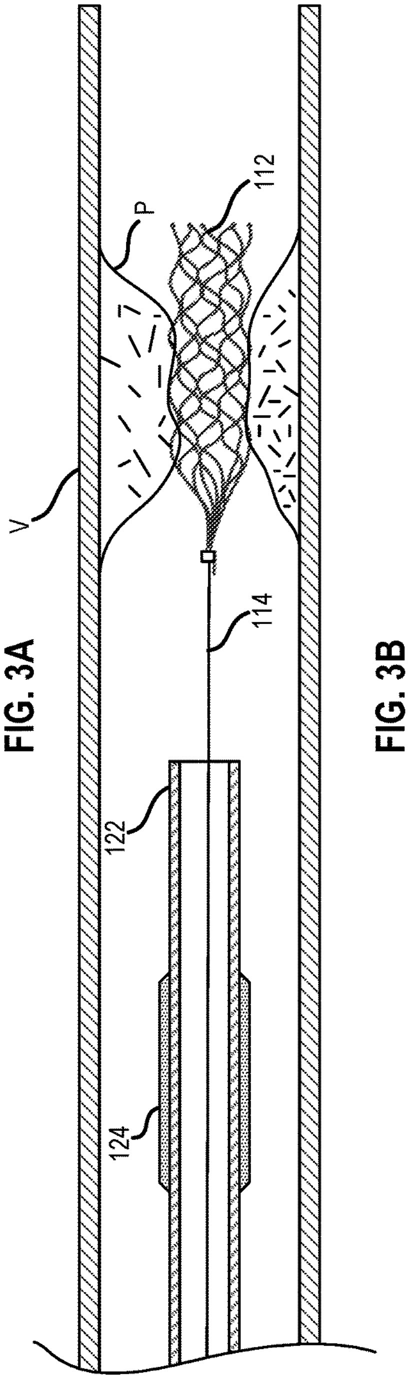

In FIG. 3B, the delivery catheter 122 has been proximally retracted, permitting the thrombectomy device 112 to self-expand into the expanded configuration. In this state, the thrombectomy device 112 can expand into apposition with the plaque P and/or with the walls of the vessel V. As noted previously, in some instances the thrombectomy device 112 may fail to sufficiently restore blood flow, and accordingly the use of an angioplasty device such as expandable member 124 may be indicated.

Figure 3C:
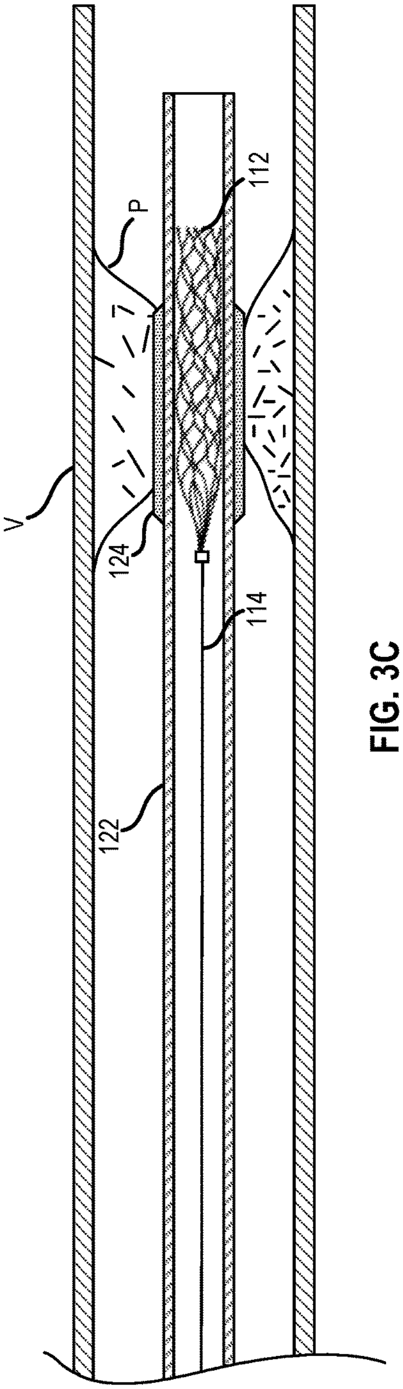

Accordingly, as shown in FIG. 3C, the clinician can deploy an angioplasty device by advancing the delivery catheter 122 over the thrombectomy device 112. As the delivery catheter 122 is distally advanced over the thrombectomy device 112, the thrombectomy device 112 is received into the delivery catheter lumen, and may assume a low-profile, constrained configuration to be fully disposed within the surrounding lumen. In various examples, the proximal taper of the thrombectomy device 112 can facilitate this resheathing of the thrombectomy device 112 within the delivery catheter 122.

Figure 3D:
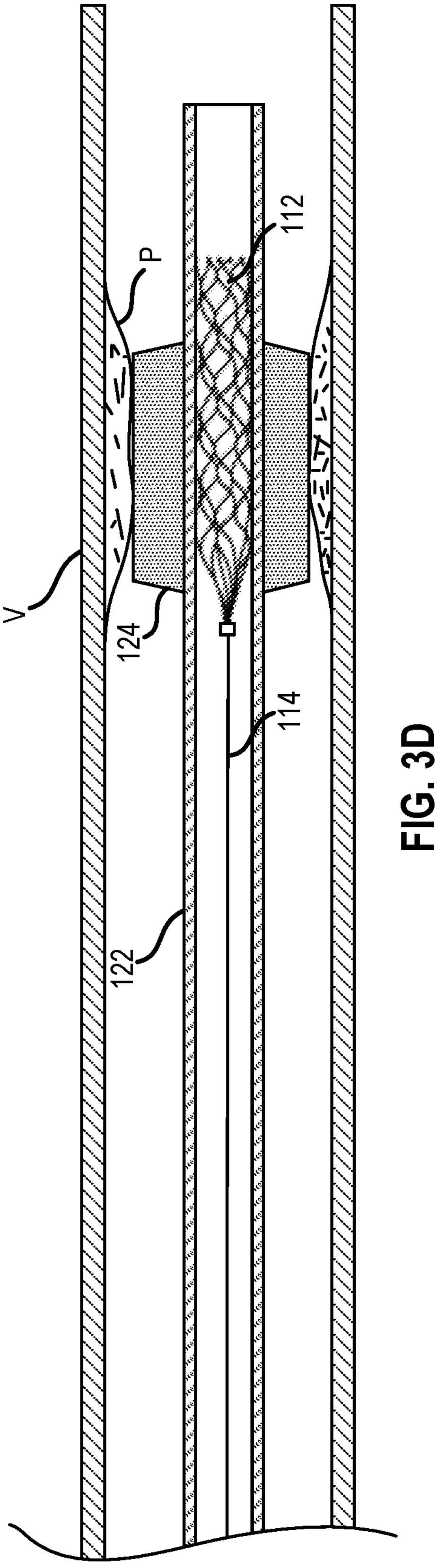
Figure 3E:
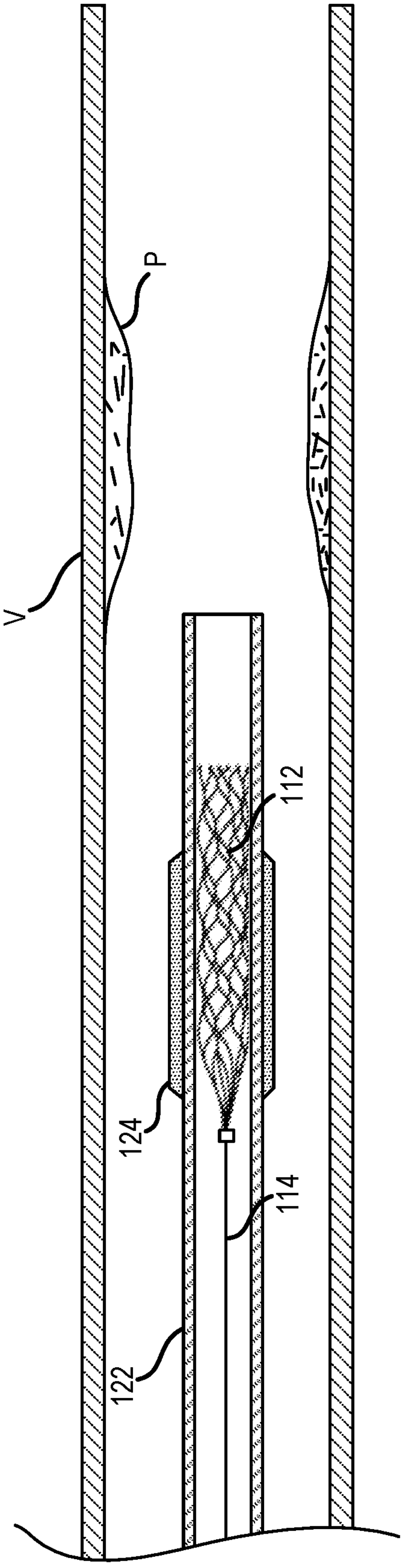

In FIG. 3D, the expandable member 124 is expanded (e.g., via an inflation lumen). This expansion can cause the plaque P to be compressed and/or displaced, thereby increasing patency of the blood vessel V. Next, as shown in FIG. 3E, the expandable member 124 can be returned to its unexpanded form (e.g., by removing fluid therefrom via the inflation lumen), and the delivery assembly and thrombectomy assembly can together be removed by proximally retracting them through the blood vessel V.

Figure 4A:
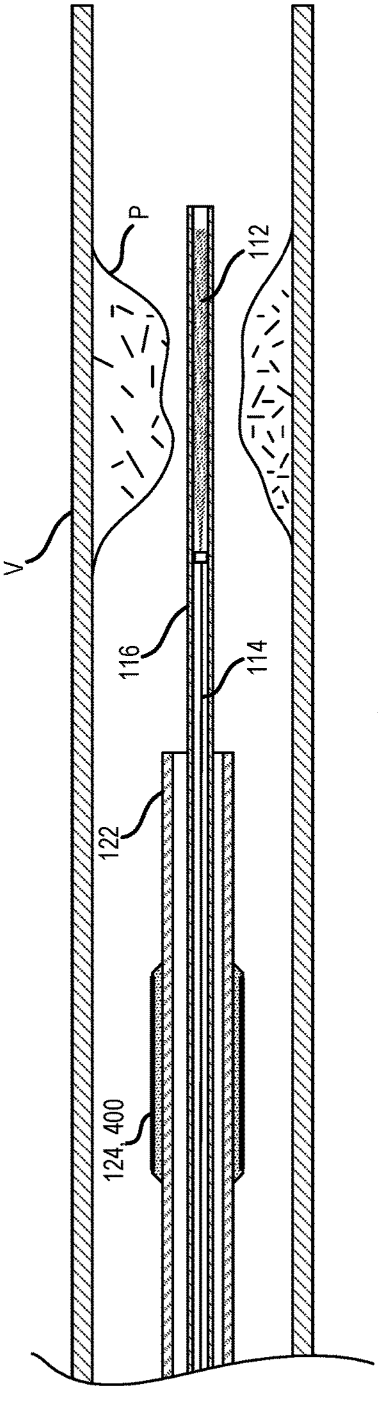
FIGS. 4A-4E show side cross-sectional views of using a treatment system to restore patency to a blood vessel in accordance with embodiments of the present technology.

FIGS. 4A-4E illustrate another method of restoring patency to a blood vessel V using the treatment system 100 of the present technology. In the method shown in FIGS. 4A-4E, the expandable member 124 includes an implant 400 (e.g., a tubular stent) configured to be implanted at the treatment site. For example, the expandable member 124 can take the form of a balloon that carries implant 400 (e.g. a balloon-mounted stent). The implant 400 assumes a low-profile, constrained configuration as shown in FIG. 4A, for instance radially constrained and in contact with the uninflated expandable member 124.

Figure 4B:
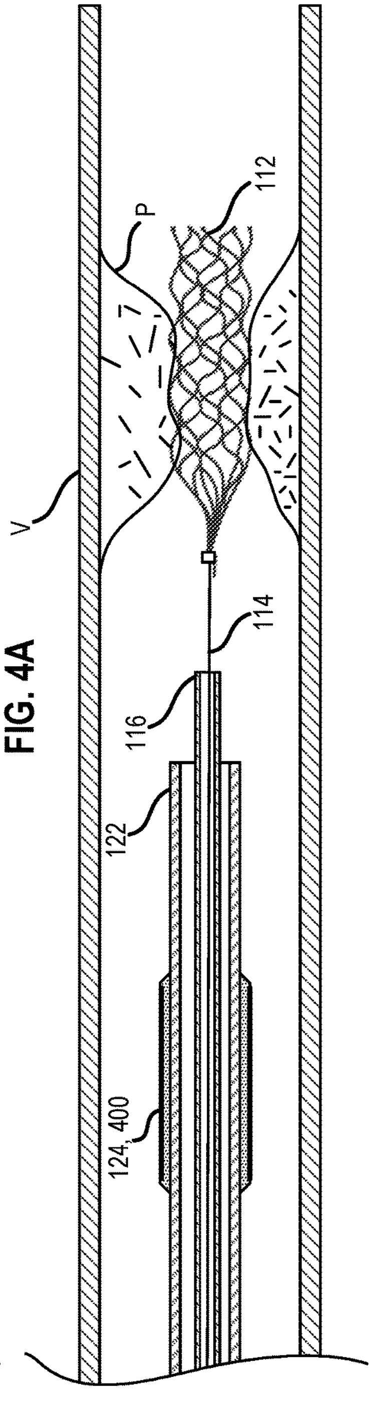
Figure 4C:
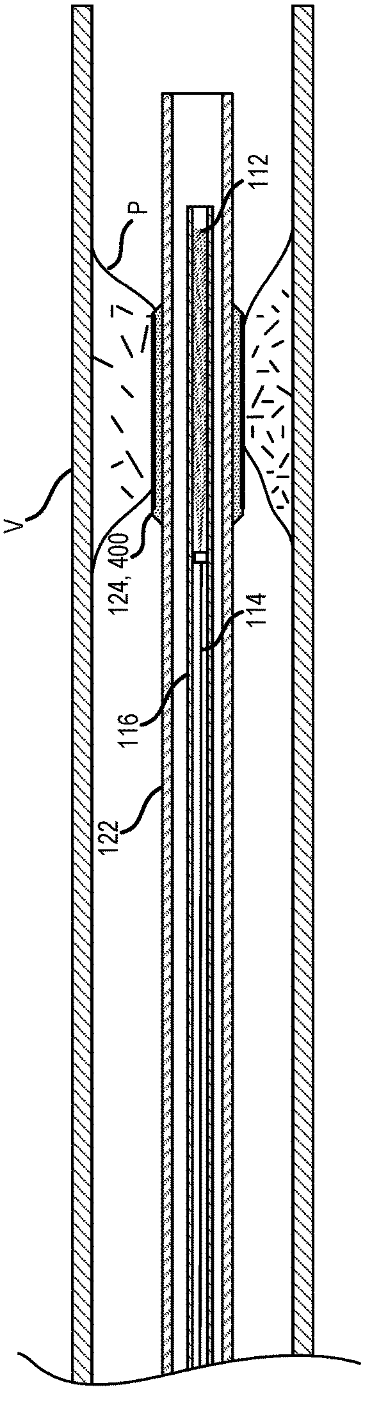
Figure 4D:
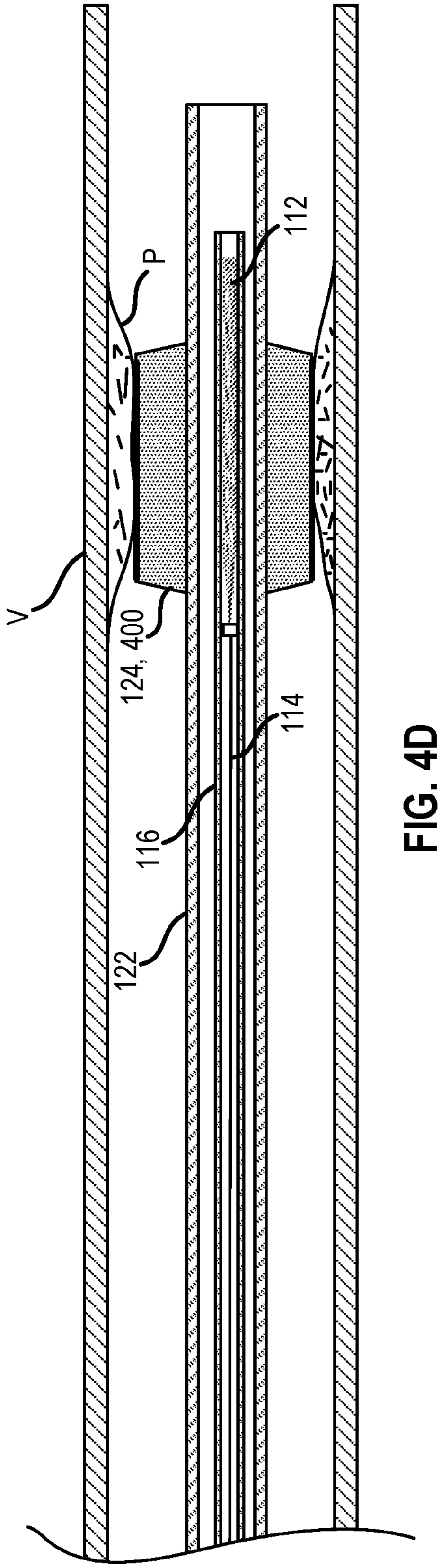
Figure 4E:
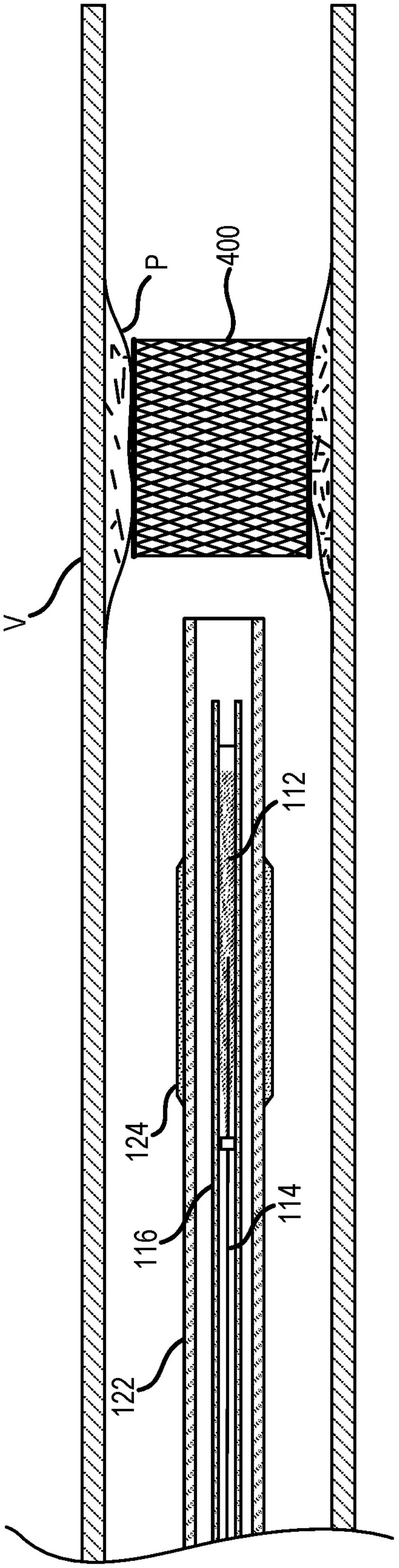

The steps shown in FIGS. 4A-4C can proceed as described above with respect to FIGS. 2A-2C. However, as shown in FIG. 4D, expansion of the expandable member 124 at the treatment site also causes the implant 400 to be expanded into contact with the plaque P. When the expandable member 124 is returned to its unexpanded state (e.g., deflated by removal of fluid therefrom), the implant 400 may remain at the treatment site, as shown in FIG. 4E. The delivery catheter assembly and the thrombectomy assembly can then be removed from the body (e.g., by proximal retraction through the blood vessel V), and the implant 400 can remain in place at the treatment site. In various implementations, the implant 400 can be configured to remain permanently within the body, and/or may be biodegradable such that the implant degrades and/or is absorbed over time.

In each of the methods illustrated in FIGS. 2A-4E, one or more optional processes may be performed before, during, and/or after deployment of the thrombectomy device 112 and/or the expandable member 124. For example, in some methods of the present technology, a fluid may be delivered to the treatment site before, during, or after deployment of the thrombectomy device 112 and/or the expandable member. Additionally or alternatively, it may be especially beneficial to arrest flow (e.g., via a flow arrest element on the guide catheter 140 and/or the delivery catheter 122) before during, or after deployment of the thrombectomy device 112 and/or the expandable member. Additionally or alternatively, in some instances aspiration may be applied to the treatment site via an aspiration catheter. For example, before, during, or after deployment of the thrombectomy device 112 and/or the expandable member 124, the treatment site can then be aspirated via the guide catheter 140, the delivery catheter 122, and/or another catheter.

III. Conclusion

Although many of the embodiments are described herein with respect to devices, systems, and methods for treating a cerebral or intracranial embolism, other applications and other embodiments in addition to those described herein are within the scope of the technology. For example, the systems and methods of the present technology may be used to remove emboli from body lumens other than blood vessels (e.g., the digestive tract, etc.) and/or may be used to remove emboli from blood vessels outside of the brain (e.g., pulmonary, abdominal, cervical, or thoracic blood vessels, or peripheral blood vessels including those within the legs or arms, etc.). In addition, the systems and methods of the present technology may be used to remove luminal obstructions other than clot material (e.g., plaque, resected tissue, foreign material, kidney stones, etc.).

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

The invention claimed is:

1. A method comprising:

providing a treatment system comprising:

a delivery catheter assembly comprising:

a tubular member defining a lumen and a distal opening and configured to be positioned intravascularly at or adjacent a treatment site; and an expandable member coupled to an outer surface of the tubular member, the expandable member configured to be expanded into apposition with a wall of a vessel at the treatment site to increase patency of the vessel at the treatment site; and a thrombectomy assembly comprising:

a core member disposed within the tubular member lumen, wherein the core member and tubular member are configured to slide relative to each other; and a thrombectomy device coupled to a distal end portion of the core member, wherein the thrombectomy assembly is configured to be slidably transitioned between a delivery configuration in which the distal end portion of the core member and the thrombectomy device are positioned within the lumen of the tubular member, and a deployed configuration in which the distal end portion of the core member and the thrombectomy device are positioned outside of the lumen of the tubular member;

disposing the thrombectomy device within the vessel such that the thrombectomy device is at or adjacent the treatment site, wherein the core member extends through the lumen of the tubular member and the thrombectomy device is disposed distal to the distal opening of the tubular member;

moving the tubular member and/or the core member to position the thrombectomy device within the tubular member lumen; and after positioning the thrombectomy device within the tubular member lumen, expanding the expandable member carried by the tubular member into apposition with the vessel wall at the treatment site.

2. The method of claim 1, wherein moving the tubular member and/or the core member comprises proximally retracting the core member relative to the tubular member.

3. The method of claim 1, wherein moving the tubular member and/or the core member comprises distally advancing the tubular member relative to the core member.

4. The method of claim 1, wherein the thrombectomy device is configured to be disposed distal to the distal opening of the tubular member in an expanded state, and wherein the thrombectomy device is configured to be positioned within the tubular member lumen in a low-profile state.

5. The method of claim 1, wherein expanding the expandable member comprises inflating an angioplasty balloon.

6. The method of claim 1, wherein expanding the expandable member comprises inflating a balloon to deploy a balloon-mounted stent at the treatment site.

7. A method comprising:

providing a treatment system comprising:

a delivery catheter assembly comprising:

a tubular member defining a lumen and a distal opening and configured to be positioned intravascularly at or adjacent a treatment site; and an expandable member coupled to an outer surface of the tubular member, the expandable member configured to be expanded into apposition with a wall of a vessel at the treatment site to increase patency of the vessel at the treatment site; and a thrombectomy assembly comprising:

a core member disposed within the tubular member lumen, wherein the core member and tubular member are configured to slide relative to each other; and a thrombectomy device coupled to a distal end portion of the core member, wherein the thrombectomy assembly is configured to be slidably transitioned between a delivery configuration in which the distal end portion of the core member and the thrombectomy device are positioned within the lumen of the tubular member, and a deployed configuration in which the distal end portion of the core member and the thrombectomy device are positioned outside of the lumen of the tubular member;

expanding the thrombectomy device at the treatment site within the vessel at the treatment site;

after expanding the thrombectomy device, moving the thrombectomy device to a collapsed configuration within the tubular member lumen while the tubular member is disposed within the vessel, thereby positioning the expandable member carried by the tubular member at the treatment site; and after moving the thrombectomy device to within the tubular member lumen, expanding the expandable member carried by the tubular member into apposition with the vessel wall at the treatment site, thereby increasing patency of the vessel at the treatment site.

8. The method of claim 7, further comprising, after expanding the expandable member, removing the tubular member and the thrombectomy device from the vessel.

9. The method of claim 7, wherein moving the thrombectomy device to the collapsed configuration comprises proximally retracting the core member relative to the tubular member.

10. The method of claim 7, wherein moving the thrombectomy device to the collapsed configuration comprises distally advancing the tubular member relative to the core member.

11. The method of claim 7, wherein the thrombectomy device is configured to be disposed distal to the distal opening of the tubular member in an expanded state, and wherein the thrombectomy device is configured to be positioned within the tubular member lumen in a low-profile state.

12. The method of claim 7, wherein expanding the expandable member comprises inflating an angioplasty balloon.

13. The method of claim 7, wherein expanding the expandable member comprises inflating a balloon to deploy a balloon-mounted stent at the treatment site.

14. A method comprising:

expanding a mechanical thrombectomy device at a treatment site within a blood vessel;

after expanding the mechanical thrombectomy device, moving the mechanical thrombectomy device to a collapsed configuration within a lumen of a catheter disposed within the blood vessel; and after moving the mechanical thrombectomy device to within the catheter lumen and while the mechanical thrombectomy device remains within the catheter lumen, expanding an expandable device coupled to an outer surface of the catheter into apposition with a wall of the blood vessel at the treatment site, thereby increasing patency of the blood vessel at the treatment site.

15. The method of claim 14, wherein moving the thrombectomy device to within the catheter lumen comprises proximally retracting the thrombectomy device relative to the tubular member.

16. The method of claim 14, wherein moving the thrombectomy device to within the catheter lumen comprises distally advancing the catheter relative to the thrombectomy device.

17. The method of claim 14, wherein the thrombectomy device is configured to be disposed distal to the distal opening of the catheter in an expanded state, and wherein the thrombectomy device is configured to be positioned within the catheter lumen in a low-profile state.

18. The method of claim 14, wherein expanding the expandable device comprises inflating an angioplasty balloon.

19. The method of claim 14, wherein expanding the expandable device comprises inflating a balloon to deploy a balloon-mounted stent at the treatment site.

* * * * *